United States Patent [19]

Hardin et al.

[11] Patent Number: 5,130,249
[45] Date of Patent: Jul. 14, 1992

[54] GALACTOMANNAN POLYSACCHARIDE PRODUCING ORGANISM

[75] Inventors: Robert S. Hardin, San Diego, Calif.; James H. Flatt; Douglas C. Cameron, both of Madison, Wis.

[73] Assignee: Wisconsin Alumni Research Foundation, Madison, Wis.

[21] Appl. No.: 526,473

[22] Filed: May 21, 1990

[51] Int. Cl.$^5$ .................... C12N 1/20; C12P 19/00; C08B 37/00
[52] U.S. Cl. .................... 435/252.1; 435/847; 435/101; 536/123; 536/114
[58] Field of Search ............ 336/123, 114, 119, 1.1; 435/252.2, 878, 101, 104, 252.1, 847; 536/123, 114

[56] References Cited

U.S. PATENT DOCUMENTS

| | | | |
|---|---|---|---|
| 3,933,788 | 1/1976 | Kang et al. | 435/101 |
| 4,073,653 | 2/1978 | Lindroth et al. | 536/59 |
| 4,384,044 | 5/1983 | Kim et al. | 435/101 |
| 4,400,466 | 8/1983 | Azoulay | 435/101 |
| 4,535,153 | 8/1985 | Kang et al. | 536/123 |
| 4,576,915 | 3/1986 | Harada et al. | 435/101 |
| 4,851,235 | 7/1989 | Schwartz et al. | 426/33 |

OTHER PUBLICATIONS

Gherna et al., *ATCC Catalogue of Bacteria and Phages*, pp. 12-13, 22-23, 41, 43-44, 105, 112, 165-184, 259-263 and 265.
*Bergey's Manual of Systematic Bacteriology*, pp. 141-159, 199-203, 210-211, 214-215, 220-221, 230-231, 240-248 and 311-316, (vol. 1), 1984.
Morris, V. J., 1987, "New and Modified Polysaccharides," in *Food Biotechnology*, (Kiny, R. D. and P. S. J. Cheetham, EDS.), pp. 193-248.
Wells, J., 1977, "Extracellular Microbial Polysaccharides-A Critical Overview," in *Extracellular Microbial Polysaccharides*, (Sanford, P. A. and Laskin, EDS.), ACS Symposium 45, pp. 299-313.
Cottrell, I. W., 1980, "Industrial Potential of Fungal and Bacterial Polysaccharides," in *Fungal Polysaccharides*, (Sanford, P. A. and K. Matsuda, EDS.), ACS Symposium 126, pp. 251-270.
Sutherland, I. A. and J. Williamson, 1979, "A Yellow Polysaccharide-Producing Bacterium With Unusual Characteristics," *European J. Appl. Microbiol.*, 6, pp. 233-240.

*Primary Examiner*—Ronald W. Griffin
*Assistant Examiner*—Pamela S. Webber
*Attorney, Agent, or Firm*—Andrus, Sceales, Starke & Sawall

[57] ABSTRACT

A galactomannan heteropolysaccharide is prepared by fermentation of a previously unknown microorganism, named Erwina sp. ATCC No. 55046. The polysaccharide has valuable properties as a thickening, suspending, stabilizing and lubricating agent in aqueous systems. It has a chemical composition of mannose, galactose and galacturonic acid in the approximate molar ratio of 5:3:2. The polysaccharide can be produced in high yield and volumetric productivity from a submerged culture fermentation of a low-cost, lactose-containing whey or whey permeate medium.

3 Claims, 9 Drawing Sheets

GALACTOMANNAN POLYSACCHARIDE PRODUCING ORGANISM

FIELD OF THE INVENTION

The present invention is directed to a method for the production of a heteropolysaccharide, having useful properties, from a pure culture of a certain Erwinia microorganism derived from a lactose-containing environment.

DESCRIPTION OF THE PRIOR ART

Polysaccharides have extensive use in both food and non-food applications primarily as a result of their ability to modify the rheology, i.e., flow behavior, of aqueous systems. Examples of uses for polysaccharides include dispersants, thickeners, film forming agents, water retention agents, coagulants, colloids, lubricant/friction reducers as well as others.

Commercially valuable polysaccharides are obtained by either recovery of gums from botanical sources, e.g., seaweeds, tree exudates, and plant seeds, or microbial fermentation broths, e.g., xanthan gum from fermentation of hydrolyzed corn syrup by *Xanthomonas campestris*. The process of production and recovery from fermentation broths generally involves the following steps:

a. aerobic fermentation of a complex medium containing a carbohydrate source, nitrogen source, trace metals and salts and vitamins;
   b. pasteurization to kill the microorganisms;
   c. pH adjustment and addition of a short-chain, aliphatic alcohol with or without salt to precipitate the polysaccharide and cellular matter;
   d. recovery and drying of the precipitate; and
   e. milling of the precipitate to achieve the desired polysaccharide texture and solubilization properties.

Microbial polysaccharides which possess these characteristics are well known and described in the prior art. Examples include the following patents. U.S. Pat. No. 4,384,044 to Kim et al. discloses a design for a bioreactor for the generic production of microbial polysaccharides from microorganisms supported on a porous, inner support. Examples of microorganisms include the genus *Rhizobium*, and particularly *Rhizobium meliloti*. The polysaccharide produced contains glucose, galactose and pyruvate in the following molar proportions: 7:1:1. U.S. Pat. No. 4,851,235 to Schwartz et al. discloses the production of food and cosmetic grade emulsifying agents by fermenting whey with a microorganism (*Candida lipolytica*). Whey is disclosed as an economical source of fermentable substrates. U.S. Patent No. 4,400,466 to Azoulev is directed to a bioreactor system for the continuous production of a *Rhizobium* microorganism to produce a thickening agent. U.S. Pat. No. 4,576,915 to Harada et al. is directed to the production of cyclic polysaccharides from novel strains of *Rhizobium phaseoli*. U.S. Pat. No. 4,535,153 to Kano et al. is directed to the production of polysaccharides by novel species of Pseudomonas.

While there exist systems for the production of polysaccharides from microbial agents, many of these systems require the use of expensive culture mediums. It would be therefore be beneficial to develop a system for the production of a useful polysaccharide which could be developed by culturing a microorganism on a more economical medium.

A proposed culture medium would have as a main ingredient whey or whey permeate. Dairy whey is a waste product of cheese production. Whey permeate, or deproteinized whey, is produced by the ultrafiltration of whey. It contains a very low concentration of milk solids and a high concentration of lactose. The effective use, or alternatively the disposal, of whey is generally an energy intensive, expensive procedure. Currently, one-half of all whey produced worldwide is disposed of by treatment in municipal sewage facilities or spreading on farm fields. It would therefore be desirable to develop a method of utilizing whey in order to produce a useful product.

SUMMARY OF THE INVENTION

It is an object of the present invention to produce a novel heteropolysaccharide with commercially-beneficial properties in an economically-recoverable quantity.

It is another object of the present invention to produce a novel heteropolysaccharide from a lactose-utilizing microorganism.

It is still further an object of the present invention to produce a novel galactose-containing polysaccharide from a microorganism which can be cultured in whey.

These objects and others are addressed by the present invention which is directed to a novel microbial heteropolysaccharide from a microbial source not previously known to exist. For purposes of the present invention, the terms "polysaccharide," "heteropolysaccharide" and "gum" will be used interchangeably.

The present invention is also directed to a substantially biologically pure culture of a microorganism, named Erwinna sp. having identifying characteristics of ATTC No. 55046, wherein the culture is capable of producing an anionic galactomannan polysaccharide in recoverable quantity upon fermentation in whey.

The present invention is also directed to a heteropolysaccharide composition, which is primarily a carbohydrate, having a most probable composition of mannose, galactose and galacturonic acid in the approximate molar ratio of 5:3:2.

The present invention is also directed to a heteropolysaccharide composition prepared by fermentation under controlled conditions of substantially biologically pure culture of the microorganism Erwinna sp. having identifying characteristics of ATTC No. 55046.

The heteropolysaccharide obtained by the fermentation of the novel microorganism described herein is stable in a variety of environments and at a variety of temperatures. It has good suspension properties and has proven to be useful at relatively high shear rates. Further, the heteropolysaccharide can be produced in a time similar to the commercial bioreactor production time of xanthan, but at a potentially reduced cost relative to the production of xanthan, due to the use of whey or whey permeate. The heteropolysaccharide has utility as a uniform thickening agent, and, in particular, is useful for suspending particles and emulsions, thickening aqueous systems across a broad range of pH and temperatures, modifying the flow properties of aqueous systems due to its elastic nature, lubricating surfaces, and possibly adhering together various materials.

It will be seen in the experiments below that the polysaccharide can efficiently modify the rheology of a wide range of aqueous systems, making it potentially useful in both food and non-food applications. The microorganism of the present invention produces a substantially pure galactomannan polysaccharide when cultured in presence of lactose, a component of whey.

This provides a specific economical advantage over the production of xanthan, which cannot be economically produced on a commercial basis in a lactose or whey environment.

For purposes of the present invention, the term "whey" is defined as the fluid medium containing a very low concentration of milk solids and a high concentration of lactose. The term "whey" is also meant to include whole whey and reconstituted wheys of up to 18% solids and ultrafiltered whey referred to as "whey permeate."

The galactomannan polysaccharide of the present invention has a wide variety of uses, both in foods and in industry. In food, the galactomannan polysaccharide has applications in cheese making, including production of cottage cheese and cream cheese, and as a substitute for fat as a soluble fiber source in cheese spreads. Additionally, the galactomannan polysaccharide has applications in the making of jellies and other high sugar systems, beverages, dairy products, salad dressings, dry mixes, icings and glazes, and other food products.

In industry, the galactomannan polysaccharide is useful as a thickening, suspending, emulsifying, stabilizing, lubrication, film-forming or binding agent. Its specific uses include adhesives, pastes, building materials, cleaners and polishes, seed coatings, binders, wet-end additives and coatings for paper products, petroleum and water-well drilling muds, cosmetics, pharmaceutical suspensions and emulsions. The polysaccharide also appears to act as a lubricant, based upon tactile evaluation of aqueous polysaccharide solutions. It is expected that the gum may be especially useful in modifying the spreading and skin-feel properties of skin care and cosmetic products.

Other objects, advantages and features of the present invention will become apparent from the following specification when taken in conjunction with the accompanying drawings.

DETAILED DESCRIPTION OF THE INVENTION

Figure 1:
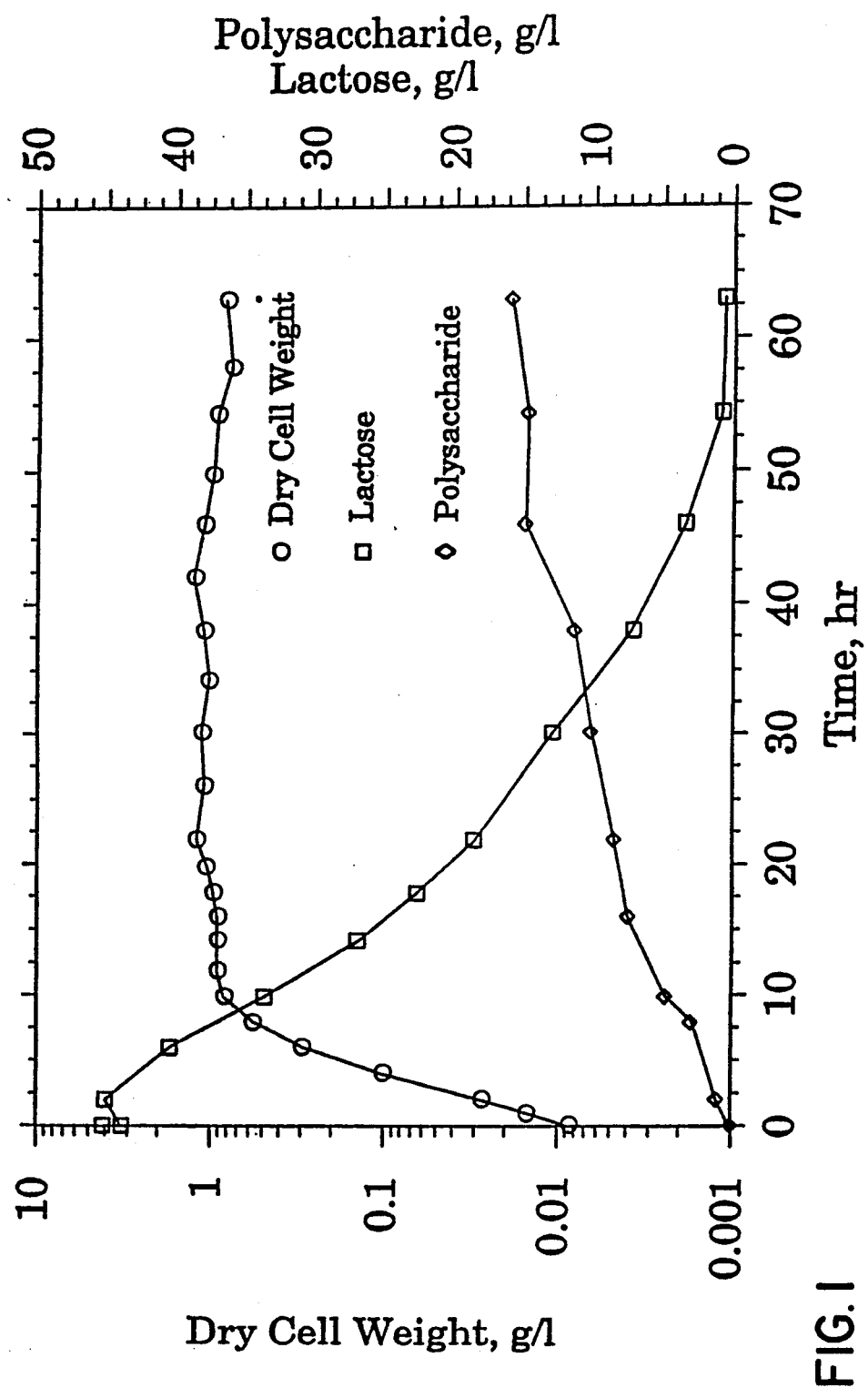
FIG. 1 is a graph illustrating the typical progress for a fermentation involving the preferred medium as described in Experiment 1 the specification.

The present invention is directed to the cultivation of a pure culture of the microorganism on a complex medium in an aerobic, submerged fermentation vessel. The particular strain of the microorganism involved in the present invention was discovered by the inventors and is identified by the following nomenclature: Erwinna sp. (E.sp). A culture of the microorganism has been deposited with the American Type Culture Collection (ATCC) on May 15, 1990, having received ATCC NO. 55046.

The polysaccharide from E.Sp. is characterized by a molecular weight of approximately $2.5 \times 10^6$. Its main building blocks are mannose and galactose, which is a component of lactose in whey. E.Sp. produces the novel galactomannan polysaccharide when cultured in presence of lactose, a component of whey, in addition to other carbohydrates.

The microorganism was isolated from a soil sample of a Wisconsin farm field near Mineral Point, WI, which had been regularly treated with whey.

The microorganism has been identified as a new species of Erwinna based on the results of extensive biochemical and microbiological tests which are summarized in the following Tables 1 and 2:

TABLE 1

| Characteristics | Erwinia sp. ATCC 55046 | Pseudomonas | Xanthomanas | Frateuria | Zooglea | Azotobacter |
|---|---|---|---|---|---|---|
| aerobic/anaerobic | +/+* | +/+** | +/− | +/− | +/+** | +/(μaero) |
| Gram-negative | + | + | + | + | + | + |
| motile | + | + | + | + | + | + |
| rod | + | + | + | + | + | + |
| soil | + | + | + | + | + | + |
| gum production | + | + | + | − | + | + |
| H$_2$S production | + | + | + | + | − | + |
| growth at pH 4 | + | − | − | + | + | − |
| growth at 37° C. | + | + | + | + | + | + |
| catalase | + | + | + | + | + | + |
| pellicle or flocs | + | − | − | − | + | |
| lipoid bodies | + | + | − | | + | − |
| 3-ketolactose | − | − | − | − | − | − |
| growth on: | | | | | | |
| lactose | + | − | + | + | + | + |
| glucose | + | + | + | + | + | + |
| fructose | + | + | + | + | | + |
| galactose | + | + | + | + | + | + |
| mannose | + | + | + | + | | |
| maltose | + | + | + | + | + | |

TABLE 1-continued

| | | | | | | |
|---|---|---|---|---|---|---|
| sucrose | + | + | + | + | + | + |
| erythritol | + | + | + | + | | |
| 2-propanol | + | + | | | | |

Notes:
+ indicates that one or more strains of the referenced genera or species possess the property
− indicates that no strains are known to possess the property
blank indicates that no information is available
μaero indicates that one or more strains are able to grow under microaerophilic conditions
*in absence of nitrate
**only in the presence of nitrate

| Characteristics | Erwinia sp. ATCC 55046 | Rhizobium | Agro-bacterium | Azomonas | Brady-rhizobium | Beijerinckia |
|---|---|---|---|---|---|---|
| aerobic/anaerobic | +/+* | +/(μaero) | +/+** | +/− | +/ | +/(μaero) |
| Gram-negative | + | + | + | + | + | + |
| motile | + | + | + | + | + | + |
| rod | + | + | + | + | + | + |
| soil | + | + | + | + | + | + |
| gum production | + | + | + | + | + | + |
| H$_2$S production | + | + | + | + | − | + |
| growth at pH 4 | + | | | | | + |
| growth at 37° C. | + | + | | + | | − |
| catalase | + | + | + | + | | + |
| pellicle or flocs | + | + | | + | | |
| lipoid bodies | + | + | | | | + |
| 3-ketolactose | − | − | + | | − | |
| growth on: | | | | | | |
| lactose | + | + | + | − | − | + |
| glucose | + | + | + | + | + | + |
| fructose | + | + | + | + | + | |
| galactose | + | + | | + | + | + |
| mannose | + | | | | | |
| maltose | + | + | + | + | − | + |
| sucrose | + | + | + | + | − | |
| erythritol | + | | + | | | + |
| 2-propanol | + | | | | | + |

Notes:
+ indicates that one or more strains of the referenced genera or species possess the property
− indicates that no strains are known to possess the property
blank indicates that no information is available
μaero indicates that one or more strains are able to grow under microaerophilic conditions
*in absence of nitrate (presence of sulfate)
**in the presence of nitrate

TABLE 2

| Characteristics | Erwinia sp. ATCC 55046 | R. legumino-sarium | R. meliloti | R. loti |
|---|---|---|---|---|
| aerobic/anaerobic | +/+ | +/(μaero) | +/(μaero) | +/(μaero) |
| Gram-negative | + | + | + | + |
| motile | + | + | + | + |
| rod | + | + | + | + |
| soil | + | + | + | + |
| gum production | + | + | + | + |
| H$_2$S production | + | − | + | − |
| growth at pH 4 | + | − | − | + |
| growth at 37° C. | + | − | + | − |
| catalase | + | | | |
| pellicle or flocs | + | | | |
| lipoid bodies | + | + | + | + |
| 3-ketolactose | − | − | − | − |

The properties of the new strain were compared with reported properties of polysaccharide-producing bacterial genera in Table 1 (Kreig,N.R. and P.H.A. Sneath, 1984, *Bergey's Manual of Systematic Bacteriology*, J.G. Holt, Editor-in-Chief, Volumes I and II). These results conclude that the microorganism is a member of the Erwinna genus. A further comparison of these test results with reported results for several species of Erwinna, listed in Table 2, indicates that the microorganism actually is a new species of Erwinna.

The microorganism grows rapidly on agar plates containing a preferred medium, which is prepared by adding 1.6% agar to the preferred liquid medium listed below in Table 3:

TABLE 3

Preferred Medium for Fermentation of Erwinia sp. ATCC 55046

| Component | Concentration (g/L) |
|---|---|
| Lactose.H$_2$O | 45.0 |
| (NH$_4$)$_2$SO$_4$ | 1.46 |
| KH$_2$PO$_4$ | 1.8 |
| K$_2$HPO$_4$ | 3.6 |
| MgSO$_4$.7H$_2$O | 0.6 |
| CaCl$_2$.2H$_2$O | 0.04 |
| FeSo$_4$.7H$_2$O | 0.0019 |
| CoCl$_2$.6H$_2$O | 0.001 |
| ZnSO$_4$.7H$_2$O | 0.001 |
| CuSO$_4$.5H$_2$O | 0.001 |
| MnSO$_4$.H$_2$O | 0.001 |
| Na$_2$MoO$_4$.2H$_2$O | 0.001 |
| Yeast Extract | 1.8 |
| NaOH | to pH 7 (roughly 0.18 g/l) |

Colonies approximately 1 mm in diameter can be observed within 24 hours after streaking the plates with a viable pure culture of the microorganism. After 48 hours, the colonies are definitely mucoid, having a whitish center surrounded by a clear matrix of viscous, and somewhat elastic material. The mound is several millimeter in height. The clear matrix continues to spread across the plate over time. After an extended period of time, the colonies will exhibit a tannish, straw-like appearance.

The novel galactomannan polysaccharide recovered by the fermentation process, which involves centrifugation, precipitation with a short-chain alcohol and optionally a salt solution, ultrafiltration or ion exchange or dialysis, and vacuum drying or lyophilization, has useful properties, primarily for modification of the rheology of aqueous solutions.

The galactomannan polysaccharide produced from the E.Sp. culture has a composition of 47-50% mannose, 27-30% galactose, 18-23% galacturonic acid and 0-4% glucose, based upon HPLC and 500 MHz proton NMR analysis of the trifluoroacetic acid hydrolysis products. The polysaccharide has a most probable composition of mannose, galactose and galacturonic acid in the approximate molar ratio of 5:3:2. Because of its composition, the novel polysaccharide is referred to as a "galactomannan polysaccharide."

The galactomannan polysaccharide was hydrolyzed in 1M trifluoroacetic acid for 1 hour at 121° C. in a nitrogen atmosphere. The neutral sugars were identified by comparison with authentic sugar standards using HPLC involving a cation exchange resin in the lead or calcium form. The ionic sugar was identified by comparison with authentic sugar standards using HPLC involving a cation exchange resin in the hydrogen ion form. These identifications were confirmed by 500 MHz proton NMR analysis relative to authentic sugar standards and enzymatic determination of galactose using the galactose oxidase enzyme.

The galactomannan polysaccharide is produced from a range of carbohydrate materials, with lactose, sucrose and maltose being preferred, and lactose being most preferred due to the combination of high yield, good productivity and low cost of the substrate.

The weight-average molecular weight of the galactomannan polysaccharide is estimated to be $2.5 \times 10^6$ daltons with a polydispersity ($M_w/M_n$) of 1.1 as measured by high performance gel permeation chromatography relative to high molecular weight dextran and xanthan standards.

The steady shear viscosity properties of the galactomannan polysaccharide primarily depend upon the concentration of polysaccharide used, the type and concentration of salts present and pH of the solution. Viscosity measurements, shown in FIGS. 3-8 and discussed in Experiments 3-6, were performed on a Wells-Brookfield RV Cone and Plate Viscometer (Brookfield Engineering Laboratories, Stoughton, MA).

The galactomannan polysaccharide is produced during the aerobic fermentation of E.Sp in a suitable aqueous medium under controlled conditions. The medium contain carbon and nitrogen sources, inorganic salts and vitamins. The types of media described are intended to be illustrative of a variety of examples of media, and are not intended to be limiting in any way.

A monosaccharide, disaccharide, oligosaccharide or mixture thereof can be used as the carbon source in the culture medium. For example, suitable carbon sources can include glucose, fructose, maltose, sucrose, xylose, mannitol, lactose or the like. Lactose is the preferred carbohydrate source. The quantity of carbohydrate source in the medium depends in part upon the ingredients in the medium. Generally, the amount of carbohydrate in the medium varies between about 2.0% and 6.0% by weight of the medium. The carbon sources can be used alone or individually.

The nitrogen sources can be conventional, such as nitrates, ammonium salts, or amino acids. The nitrogen source can be a complex mixture of compounds, as is present in whey. Additionally, gaseous ammonia may be used as the source, and may be preferable for practical and economic reasons.

Inorganic salts, vitamins and other ingredients, which are essential for the proper growth of the microorganism, are also added to the medium. The ingredients are those customary to the trade and include, without limitation, sodium, potassium, ammonium, calcium, phosphate, sulfate, chloride, carbonate, and like ions. Also included may be trace metals such as cobalt, manganese, iron and magnesium.

The fermentation is carried out at temperatures ranging from about 20° C. to 32° C., preferably 24°C.-27°C. Higher or lower temperatures may be possible, but above 34° C., the galactomannan polysaccharide yield generally decreases. The pH of the nutrient medium for growing the culture and producing the galactomannan polysaccharide can vary from about 6 to 8.

The fermentation can be carried out as either a batch or continuous process under submerged conditions in a suitable fermenter. It is within the scope of the present invention to scale up the fermentation process to industrial conditions or to scale down the process to experimental conditions according to steps known to the art.

The following non-limitative experiments are designed to illustrate the present invention.

EXPERIMENT 1

Preferred Method of Production of Galactomannan Polysaccharide

The preferred method of producing the galactomannan polysaccharide of the present invention entails the aerobic fermentation of the E.Sp. microorganism using fast agitation (800 rpm in a 5 liter vessel) and a high rate of air sparging (roughly 1 vol. air per vol. broth per min.) in a medium containing a high carbon-to-nitrogen ratio, trace metals and salts, and vitamins which are supplied by yeast extract (or equivalent). The preferred medium has been previously described in Table 3. The carbon-to-nitrogen ratio is very high, roughly 40:1 molar C/N ratio. The pH is held at 7 and the temperature at 26° C. It was previously discovered that raising the temperature to 34° C. decreases the yield of polysaccharide significantly.

Reference is now made to FIG. 1 which shows the typical progress for a fermentation involving the preferred medium. This fermentation was performed in a 5 liter fermenter which is reasonably representative of results which could be achieved in a production scale fermenter. The overall results indicate that the galactomannan polysaccharide can be produced with a good yield (0.38 g/g) and volumetric productivity (0.3 g/l.hr). The galactomannan polysaccharide can be recovered from the fermentation broth by the addition of sufficient quantities of a short-chain, aliphatic alcohol such as ethanol, n-propanol or isopropanol. The addition of sufficient isopropanol to achieve a 60-70% (v/v) solution of isopropanol and broth is the preferred method for crude recovery of the polysaccharide. The precipitate can then be harvested from the alcohol solution by decantation, filtration or centrifugation. Finally, the precipitate can be dried and milled to achieve the desired consistency of the final product.

The cell mass may be nearly completely removed by modification of the above recovery procedure. First, the crude precipitate is resuspended in deionized water. This mixture is then centrifuged for 10 minutes at 25° C. and $20,000 \times g$ to cause the formation of a compact cell pellet.

The polysaccharide is removed by decantation, prior to the addition of sufficient isopropanol to achieve a 80% minimum (v/v) solution of isopropanol and broth. The precipitated polysaccharide may be desalted and deproteinized by ultrafiltration. The polysaccharide is redissolved in deionized water to a concentration of roughly 1 g/l. Continuous dilution of the polysaccharide solution with deionized water, using a total of 5 volumes of water per volume of polysaccharide solution, is required to produce a nearly salt-free solution.

EXPERIMENT 2

Carbohydrate Source Studies

Figure 2:
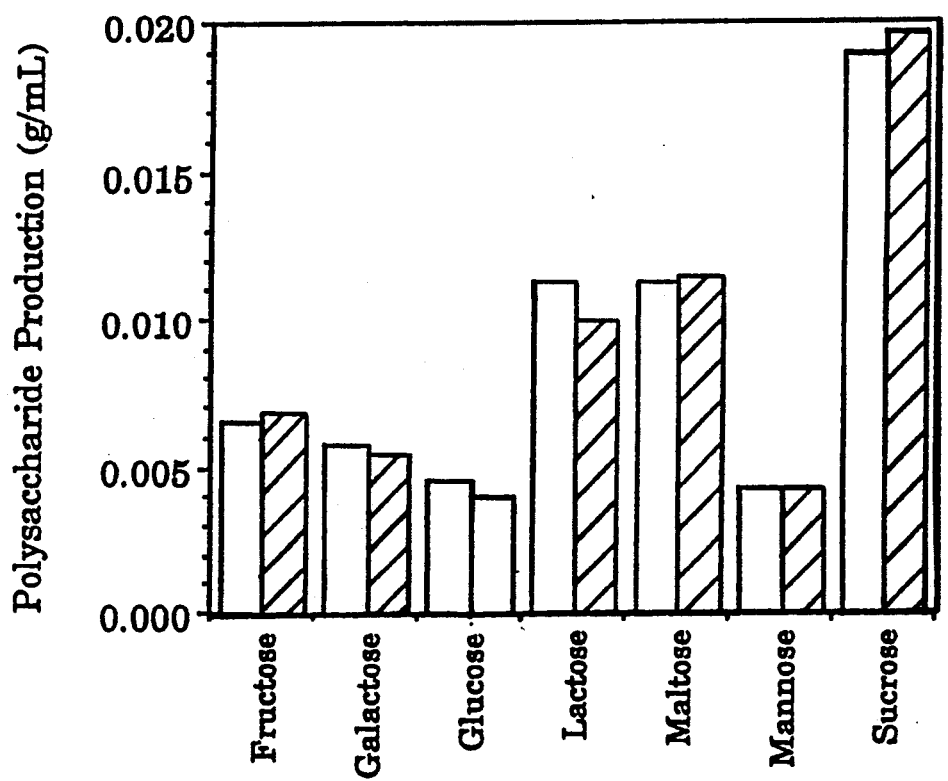
FIG. 2 is a chart illustrating the production of galactomannan polysaccharide from Erwinna sp. as a function of the carbohydrate source.

Replicate experiments were performed in 70 ml (liquid volume) shake flasks, which contained the base medium described in Experiment 1, varying only in the nature of carbohydrate material. Reference is now made to FIG. 2 for an illustration of the results of this experiment. Each bar in FIG. 2 represents the polysaccharide produced by E. Sp. on the specified sugar in each shake flask. The microorganism produces polysaccharide in the highest quantities from disaccharide carbohydrates (sucrose, lactose and maltose). Sucrose appeared to give the highest yield of polysaccharide. The polysaccharide was produced from monosaccharide carbohydrates (glucose, galactose, mannose and fructose), but in significantly reduced quantities.

Shake flask experiments using a representative whey permeate from Havarti cheese production indicated that the microorganism can produce the polysaccharide efficiently from whey. Polysaccharide production, as indicated by steady shear viscosity data, was higher on the whey medium than on the base medium described in Experiment 1. The average viscosity of 2 flasks after 144 hours at 10 sec$^{-1}$ and 25° C. was 1415 mPa.s from the whey medium versus 924 mPa.s for the base medium.

EXPERIMENT 3

Figure 3:
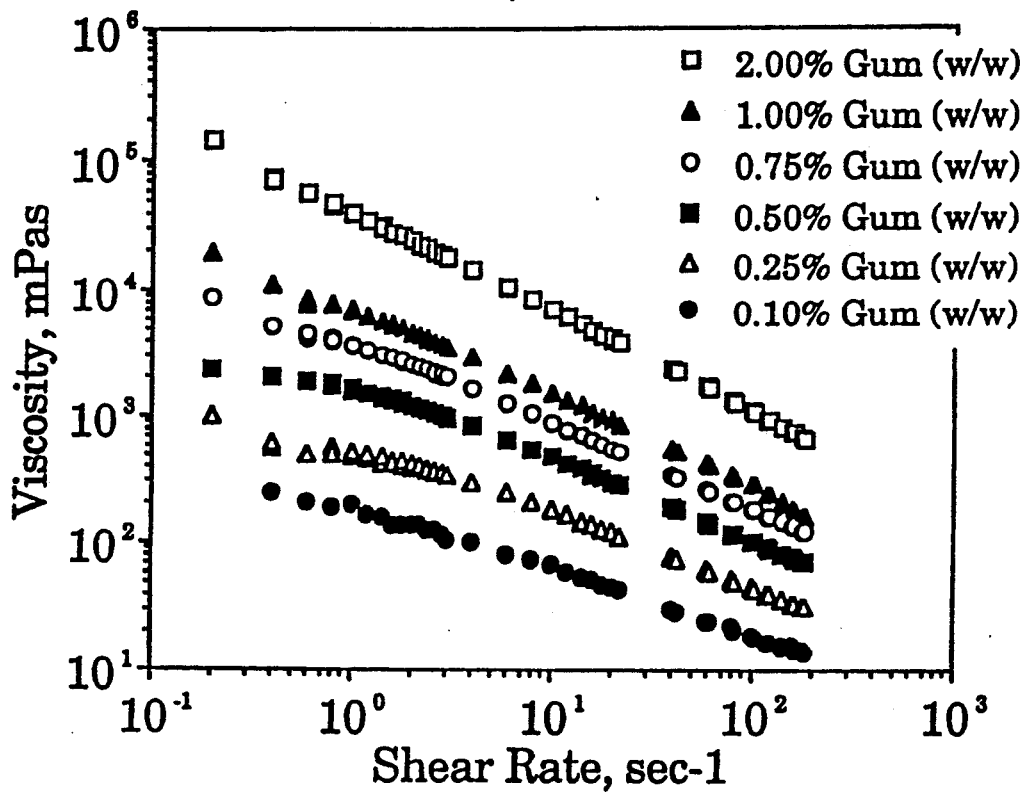
FIG. 3 is a graph illustrating the steady shear viscosity of aqueous polysaccharide solutions across a variety of concentrations and shear rates at pH 7, 25° C. and no salt present.
Figure 4:
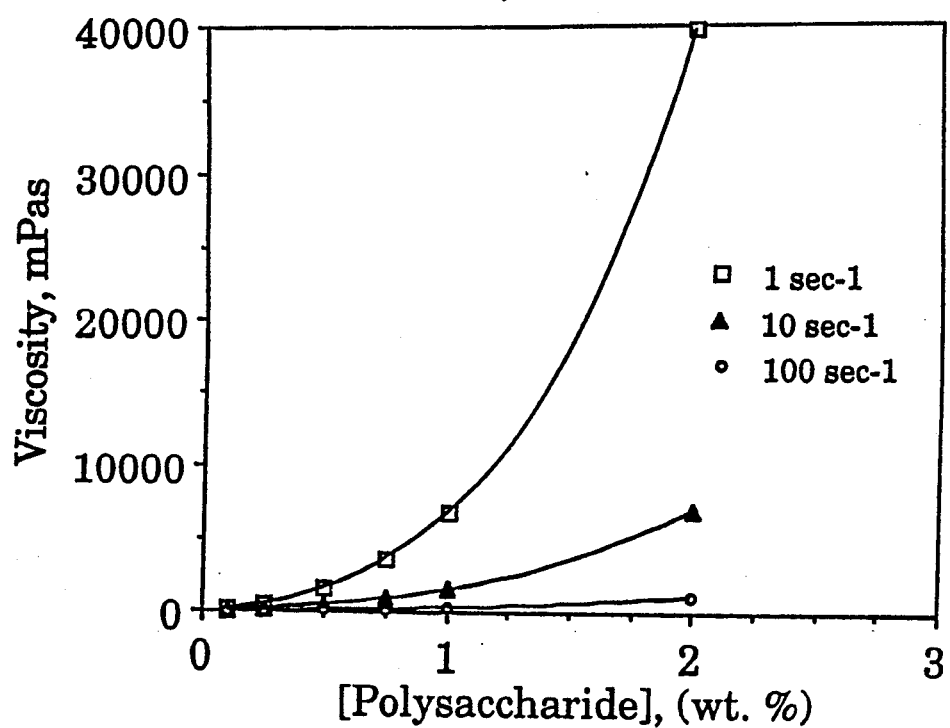
FIG. 4 is a graph illustrating the steady shear viscosity of aqueous polysaccharide solutions as a function of polysaccharide concentration.

Steady Shear Viscosity of Aqueous Polysaccharide Solutions as a Function of Gum Concentration The steady shear viscosity as a function of gum concentration is illustrated in FIG. 3 across a variety of shear rates at pH 7, 25° C. and no salt present. Aqueous polysaccharide solutions were prepared by dissolving specified amounts of purified polysaccharide in distilled, deionized water. The purified polysaccharide was produced as described in Experiment 1. The results indicate that aqueous solutions of the polymer show pseudoplastic (shear thinning) flow behavior at moderate to high shear rates ($> 1$ sec$^{-1}$) at all concentrations, but show more Newtonianlike behavior at lower shear rates ($<$sec$^{-1}$) for gum concentrations of $\leq 0.5\%$. Furthermore, this polysaccharide is a moderately efficient thickener. The viscosity of aqueous solution increases in a power-law fashion with increasing gum concentration as shown in FIG. 4.

EXPERIMENT 4

Figure 5:
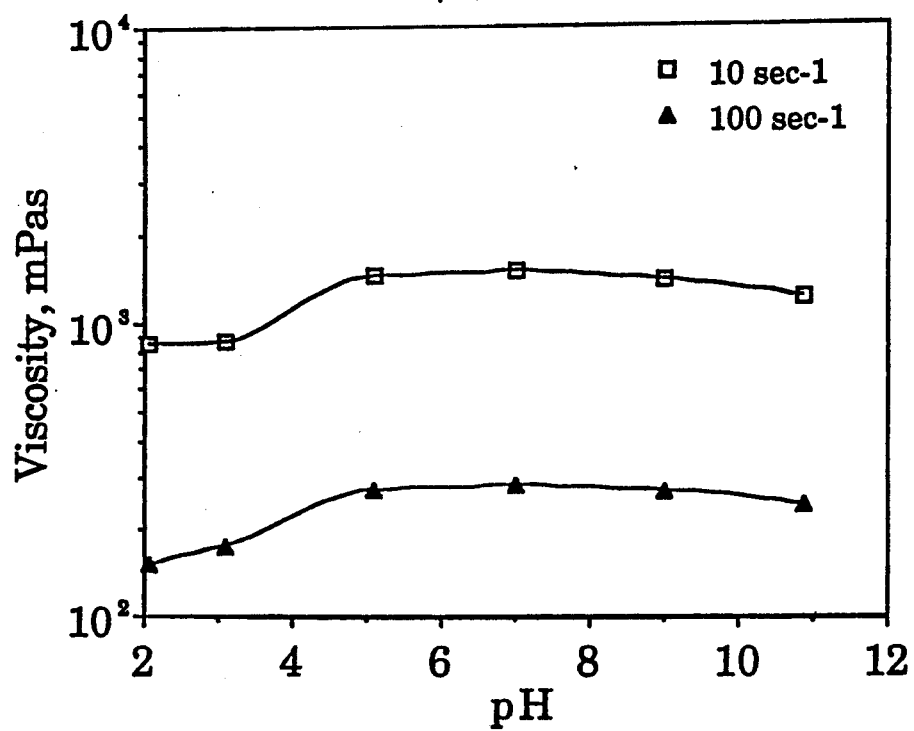
FIG. 5 is a graph illustrating the steady shear viscosity of aqueous polysaccharide solutions across a range of pH.

Steady Shear Viscosity of Aqueous Polysaccharide Solutions Across a Range of pH The steady shear viscosity across a range of pH is shown in FIG. 5. Aqueous polysaccharide solutions of specified pH were prepared by addition of varying amounts of 4N hydrochloric acid or 4N sodium hydroxide to a 1% (w/w) purified polysaccharide solution. These results indicate that the thickening properties of the polysaccharide are very stable from pH 5 to 11 and decrease only slightly from pH 5 to pH 2. Thus, consistent thickening results can be achieved in a broad range of food and non-food formulations, even as the pH of the system may 15 change with aging.

EXPERIMENT 5

Steady Shear Viscosity of Aqueous Polysaccharide Solutions as a Function of Potassium Chloride (KCl). Calcium Chloride (CaCl$_2$) and Magnesium Chloride (MoCl$_2$)

Figure 6:
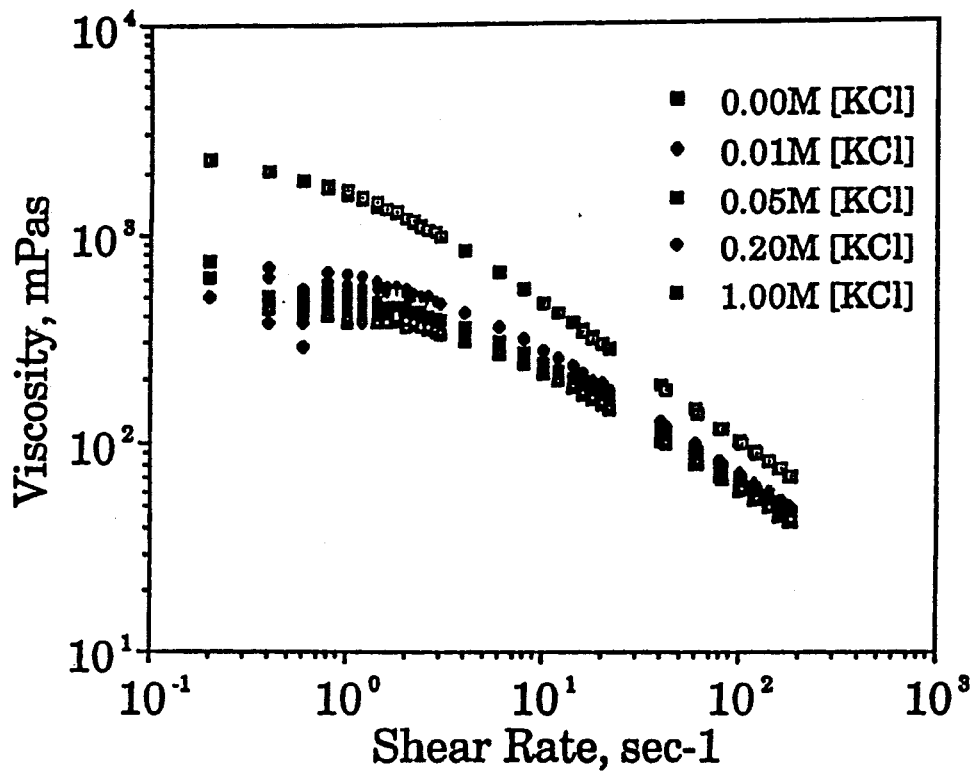
FIG. 6 is a graph illustrating the steady shear viscosity of aqueous polysaccharide solutions as a function of potassium chloride (KCl) concentration.
Figure 7:
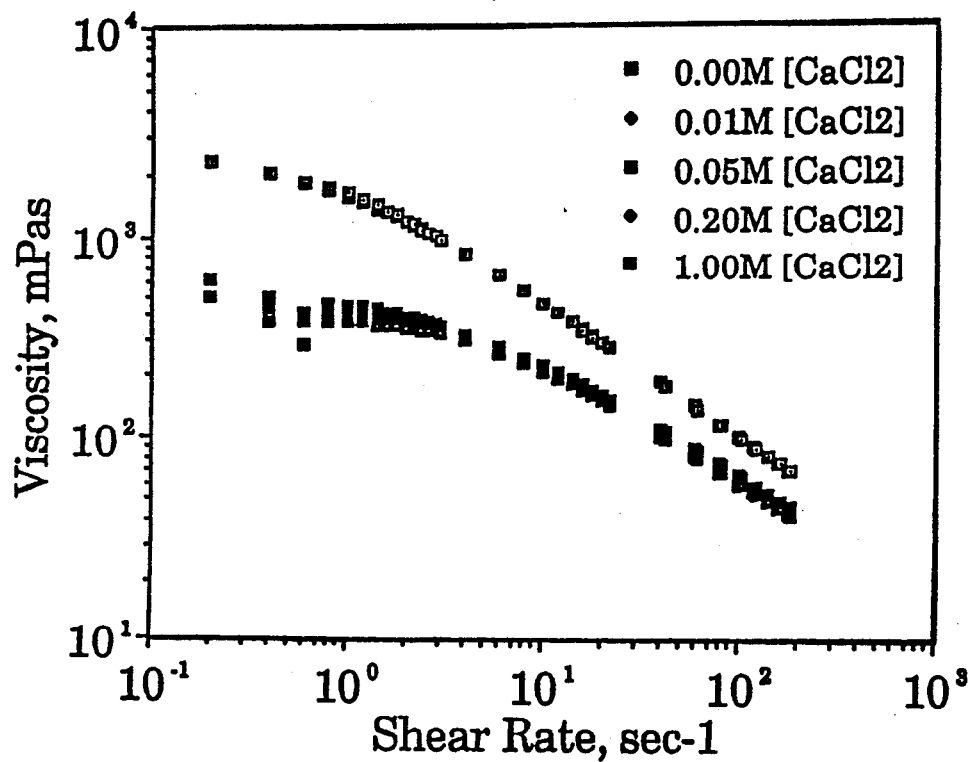
FIG. 7 is a graph illustrating the steady shear viscosity of aqueous polysaccharide solutions as a function of calcium chloride ($CaCl_2$) concentration.
Figure 8:
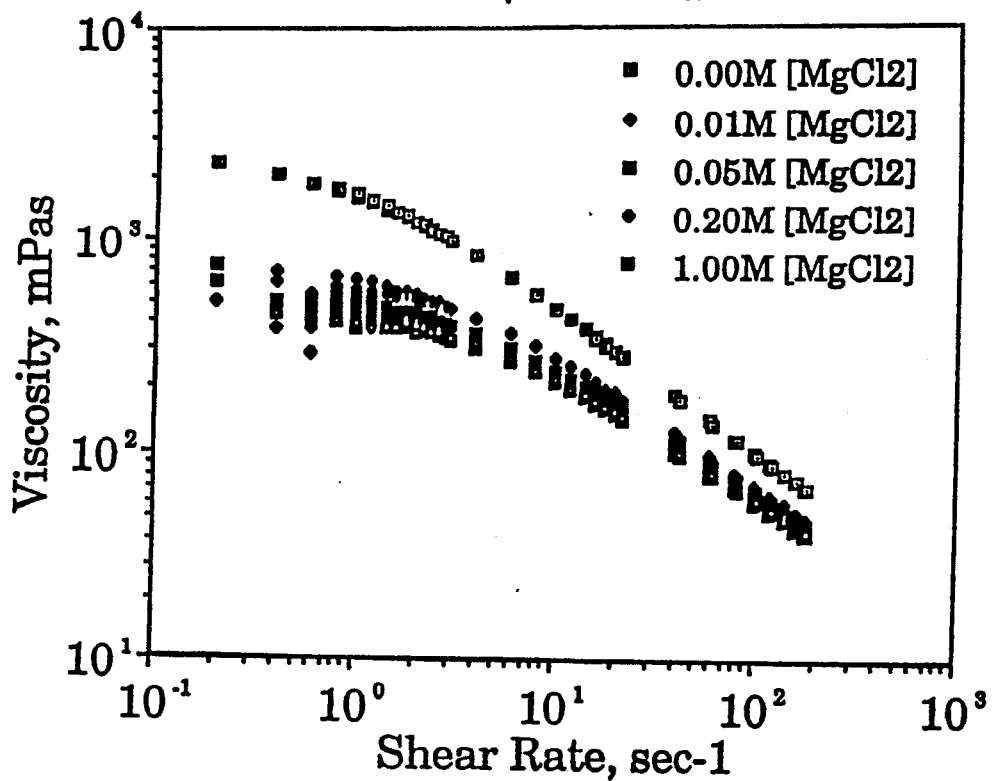
FIG. 8 is a graph illustrating the steady shear viscosity of aqueous polysaccharide solutions as a function of magnesium chloride ($MgCl_2$) concentration.

The steady shear viscosity of aqueous polysaccharide solutions as a function of potassium chloride, calcium chloride and magnesium chloride is shown in FIGS. 6-8. Aqueous polysaccharide solutions of specified salt concentrations were prepared by adding varying amounts of 2M salt solutions to a 1% (w/w) purified polysaccharide solution. Sufficient distilled, deionized water was added to bring the final polysaccharide concentration of each solution to 0.5% (w/w). These results indicate that the polysaccharide remains soluble and builds viscosity in systems containing high levels of most monovalent and divalent salts. It is important to note that viscosity generally tends to decrease as the level of salt increases, being more noticeable at lower shear rates and less noticeable at higher shear rates. Furthermore, the viscosity seems to reach a minimum at 0.05M to 0.20M total salt concentration, before increasing with the addition of more salt.

EXPERIMENT 6

Rheological Properties Imparted by the Galactomannan Polysaccharide

Figure 9:
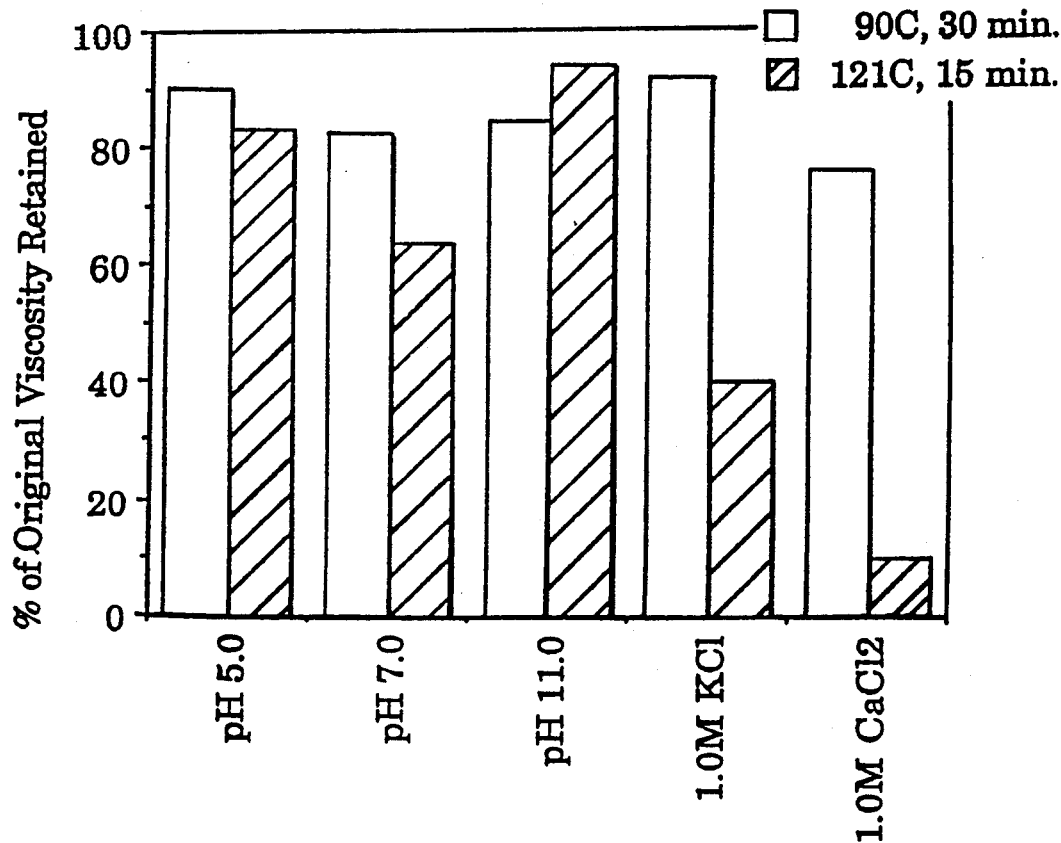
FIG. 9 is a chart illustrating the temperature stability of aqueous 1% polysaccharide solutions as a function of solution environment.

An experiment was performed in which sealed tubes of various aqueous 1% polysaccharide solutions were exposed to either 90° C. for 30 minutes or 121° C. for 15 minutes and then cooled to 25 ©C. The steady shear viscosity at 100 sec$^{-1}$ are shown in FIG. 9. The results show that the gum is very resistant to thermal degradation in alkaline environments, but less resistant to thermal degradation in high salt environments. In addition, any thermal viscosity degradation is more noticeable at lower shear rates. Resistance to thermal degradation is substantially improved in all environments when temperature exposure is limited to 90° C. In summary, the polysaccharide may provide beneficial properties for applications in which heat is involved, such as specific food applications and oil recovery and drilling applications.

The results indicate that the rheological properties imparted by the polysaccharide are relatively stable in high temperature environments up to 2°0 C. The viscosities of solutions decrease with an increase in temperature; however, upon return to the lower temperature, the solutions can rebuild most of the original viscosity, depending upon the temperature, length of exposure, solution environment and shear rate.

Aqueous polysaccharide solutions exhibit elasticity, which may be beneficial for modification of pouring or spreading properties of the solutions.

EXPERIMENT 7

Compatibility of the Polysaccharide with Short-Chain Alcohols in Aqueous Systems Solubility studies were performed by dissolving dried, purified polysaccharide in aqueous solutions containing the specified amount of alcohol. Solubility was determined by visually observing the absence of precipitate, flocs or particles in a homogeneous solution. The homogeneity of the solution was determined by measuring the difference in optical density at 660nm between the polysaccharide/alcohol solution and a reference aqueous alcohol solution containing no polysaccharide. Homogeneous solutions showed no change in optical density.

The results of solubility tests indicate that the polysaccharide forms stable, viscous solutions in the presence of various short chain alcohols. In particular, a polysaccharide up to !% concentration is completely soluble in aqueous solutions containing up to 80% (v/v) methanol, and 60% (v/v) ethanol, isopropanol and n-propanol.

It is understood that the invention is not confined to the particular construction and arrangement herein described, but embraces such modified forms thereof as come within the scope of the following claims.

What is claimed is:

1. A biologically pure strain of Erwinia sp., which produces a galactomannan polysaccharide having a composition of mannose, galactose and galacturonic acid in the approximate molar ratio of 5:3:2.

2. The strain according to claim 1, which is Erwinia sp. ATCC No. 55046.

3. A biologically pure culture of microorganism Erwinia sp. having identifying characteristics of ATCC No. 55046, said culture being capable of producing galactomannan polysaccharide in a recoverable quantity upon fermentation in whey.

* * * * *